US008592184B2

(12) United States Patent
Heindl et al.

(10) Patent No.: US 8,592,184 B2
(45) Date of Patent: Nov. 26, 2013

(54) NUCLEIC ACID AMPLIFICATION IN THE PRESENCE OF MODIFIED RANDOMERS

(71) Applicants: Dieter Heindl, Paehl (DE); Waltraud Ankenbauer, Penzberg (DE); Frank Laue, Paehl-Fischen (DE)

(72) Inventors: Dieter Heindl, Paehl (DE); Waltraud Ankenbauer, Penzberg (DE); Frank Laue, Paehl-Fischen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/711,846

(22) Filed: Dec. 12, 2012

(65) Prior Publication Data
US 2013/0109060 A1 May 2, 2013

Related U.S. Application Data

(63) Continuation of application No. 12/406,450, filed on Mar. 18, 2009, now abandoned.

(30) Foreign Application Priority Data

Mar. 19, 2008 (EP) ................................. 08005100

(51) Int. Cl.
C12P 19/34 (2006.01)
C07H 21/00 (2006.01)

(52) U.S. Cl.
USPC .......... 435/91.1; 435/6.1; 536/23.1; 536/24.3

(58) Field of Classification Search
USPC .......................... 435/6.1, 91.1; 536/23.1, 24.3
See application file for complete search history.

(56) References Cited

U.S. PATENT DOCUMENTS

| 5,118,801 | A | 6/1992 | Lizardi et al. |
| 5,210,015 | A | 5/1993 | Gelfand et al. |
| 5,338,671 | A | 8/1994 | Scalice et al. |
| 5,338,848 | A | 8/1994 | Acker et al. |
| 5,411,876 | A | 5/1995 | Bloch et al. |
| 5,449,603 | A | 9/1995 | Nielson et al. |
| 5,487,972 | A | 1/1996 | Gelfand et al. |
| 5,677,152 | A | 10/1997 | Birch et al. |
| 5,693,502 | A | 12/1997 | Gold et al. |
| 5,773,258 | A | 6/1998 | Birch et al. |
| 5,792,607 | A | 8/1998 | Backman et al. |
| 5,804,375 | A | 9/1998 | Gelfand et al. |
| 5,985,619 | A | 11/1999 | Sutherland et al. |

(Continued)

FOREIGN PATENT DOCUMENTS

| EP | 0744470 A1 | 11/1996 |
| EP | 1275735 A1 | 1/2003 |

(Continued)

OTHER PUBLICATIONS

European Search Report issued Aug. 25, 2008 in Application No. EP 08005100, 2 pages.

(Continued)

Primary Examiner — Jezia Riley
(74) Attorney, Agent, or Firm — Dinsmore & Shohl LLP

(57) ABSTRACT

The present invention is directed to a composition comprising a DNA Polymerase which is preferably thermostable, Deoxynucleotides, at least one primer oligonucleotide or a pair of amplification primers, and randomized 5-8 mer oligonucleotide, characterized in that said oligonucleotide comprises a modification with an organic hydrophobic moiety Such a composition is specifically useful for performing hot start PCR.

9 Claims, 5 Drawing Sheets

(56) References Cited

U.S. PATENT DOCUMENTS

| | | | |
|---|---|---|---|
| 6,020,130 | A | 2/2000 | Gold et al. |
| 6,174,670 | B1 | 1/2001 | Wittwer et al. |
| 6,241,557 | B1 | 6/2001 | Reichardt |
| 6,403,341 | B1 | 6/2002 | Barnes et al. |
| 6,569,627 | B2 | 5/2003 | Wittwer et al. |
| 6,667,165 | B2 | 12/2003 | Peters |
| 2003/0118992 | A1 | 6/2003 | Warren |
| 2003/0118998 | A1* | 6/2003 | Dean et al. .................... 435/6 |
| 2005/0221304 | A1 | 10/2005 | Xiang et al. |
| 2007/0238117 | A1 | 10/2007 | Rajeevan et al. |

FOREIGN PATENT DOCUMENTS

| | | |
|---|---|---|
| EP | 0799888 B1 | 5/2005 |
| GB | 2293238 A | 3/1996 |
| WO | 97/46706 A1 | 12/1997 |
| WO | 97/46707 A1 | 12/1997 |
| WO | 97/46712 A1 | 12/1997 |
| WO | 97/46714 A1 | 12/1997 |
| WO | 99/46400 A1 | 9/1999 |
| WO | 00/68411 A1 | 11/2000 |
| WO | 02/14555 A3 | 2/2002 |

OTHER PUBLICATIONS

Chakrabarti, Raj and Schutt, Clarence. E., "The enhancement of PCR amplification by low molecular weight amides," Nucleic Acids Research, 2001, pp. 2377-2381, vol. 29, No. 11.

Chou, Quin, et al., "Prevention of pre-PCR mis-priming and primer dimerization improves low-copy-number amplifications," Nucleic Acids Research, 1992, pp. 1717-1723, vol. 20, No. 7.

Dogan, Zeynep, et al., "5'-Tethered Stilbene Derivatives as Fidelity- and Affinity-Enhancing Modulators of DNA Duplex Stability," Journal of the American Chemical Society, 2004, pp. 4762-4763, vol. 126, No. 15.

Hengen, Paul N., "Optimizing multiplex and LA-PCR with betaine,"Trends in Biochemical Sciences, 1997, pp. 225-226, vol. 22.

Hildebrand, C. E., et al., "Action of Heparin on Mammalian Nuclei," Biochimica et Biophysica Acta, 1977, pp. 295-311, vol. 477.

Kaboev, O. K., et al., "Hot Start of the Polymerase Chain Reaction Using DNA Helicases," Bioorganicheskai•a•khimii•a•, 1999, pp. 398-400, vol. 25.

Kainz, Peter, et al., "Specificity-Enhanced Hot-Start PCR: Addition of Double-Stranded DNA Fragments Adapted to the Annealing Temperature," BioTechniques, 2000, pp. 278-282, vol. 28, No. 2.

Kellogg, D. E., et al., "TaqStart Antibody(TM): "Hot Start" PCR Facilitated by a Neutralizing Monoclonal Antibody Directed Against Taq DNA Polymerase," Biotechniques, 1994, pp. 1134-1137, vol. 16, No. 6.

Lin, Yun, and Jayasena, Sumedha D., "Inhibition of Multiple Termostable DNA Polymerases by a Heterodimeric Aptamer," Journal of Molecular Biology, 1997, pp. 100-111, vol. 271.

Mokhir, Andrly A. and Richert, Clemens, "Synthesis and monitored selection of 5'-nucleobase-capped oligodeoxyribonucleotides," Nucleic Acids Research, 2000, pp. 4254-4265, vol. 28, No. 21.

Moretti, Tamyra, et al., "Enhancement of PCR Amplification Yield and Specificity Using AmpliTaq Gold(TM) DNA Polymerase," Biotechniques, 1998, pp. 716-722, vol. 25, No. 4.

Narayanan, Sukunath, et al., "Clamping down on weak terminal base pairs: oligonucleotides with molecular caps as fidelity-enhancing elements at the 5'- and 3'-terminal residues," Nucleic Acids Research, 2004, pp. 2901-2911, vol. 32, No. 9.

Nilsson, J., et al., "Heat-Mediated Activation of Affinity-Immobilized Taq DNA Polymerase," Biotechniques, 1997, pp. 744-751, vol. 22, No. 9.

Sharkey, David J., et al., "Antibodies as Thermolabile Switches: High Temperature Triggering for the Polymerase Chain Reaction," Bio/Technology, 1994, pp. 506-509, No. 12.

The Stratagen Catalog, 1988, p. 39.

Stuerzenbaum, Stephen R., "Transfer RNA Reduces the Formation of Primer Artifacts During Quantitative PCR," Bio/Techniques, 1999, pp. 50-52, vol. 27, No. 1.

* cited by examiner 5a             5b 5c             5d

SEQUENCE LISTING

<160> NUMBER OF SEQ ID NOS: 13

<210> SEQ ID NO 1
<211> LENGTH: 26
<212> TYPE: DNA
<213> ORGANISM: artificial
<220> FEATURE:
<223> OTHER INFORMATION: primer

<400> SEQUENCE: 1
attagagaac catgttaaca ctaccg                26

<210> SEQ ID NO 2
<211> LENGTH: 26
<212> TYPE: DNA
<213> ORGANISM: artificial
<220> FEATURE:

<223> OTHER INFORMATION: primer

<400> SEQUENCE: 2
gaggtgaatg accactgttt attttc                                   26

<210> SEQ ID NO 3
<211> LENGTH: 23
<212> TYPE: DNA
<213> ORGANISM: artifical

<400> SEQUENCE: 3
ggaagtacag ctcagagttc tgc                                      23

<210> SEQ ID NO 4
<211> LENGTH: 27
<212> TYPE: DNA
<213> ORGANISM: artificial
<220> FEATURE:
<223> OTHER INFORMATION: primer

<400> SEQUENCE: 4
gaatctccat tcattctcaa aaggact                                  27

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
taaagggtca ccgtggcttc                                          20

<210> SEQ ID NO 6
<211> LENGTH: 18
<212> TYPE: DNA
<213> ORGANISM: artificial
<220> FEATURE:
<223> OTHER INFORMATION: primer

<400> SEQUENCE: 6
cgaaccacat tggcatca                                            18

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7 cacccccgtgc tgctgaccga                                         20

<210> SEQ ID NO 8
<211> LENGTH: 20
<212> TYPE: DNA
<213> ORGANISM: artificial
<220> FEATURE:
<223> OTHER INFORMATION: primer

<400> SEQUENCE: 8
agggaggcgg ccaccagaag                                          20

<210> SEQ ID NO 9
<211> LENGTH: 21
<212> TYPE: DNA

```
<213> ORGANISM: artificial
<220> FEATURE:
<223> OTHER INFORMATION: primer

<400> SEQUENCE: 9
tgcagcctcc ataaccatga g                                          21

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
gatgcctgcc attggaccta                                            20

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
gatgcctgcc attggaccta                                            20

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
gcaaacagag tgagcccttc                                            20

<210> SEQ ID NO 13
<211> LENGTH: 19
<212> TYPE: DNA
<213> ORGANISM: artificial
<220> FEATURE:
<223> OTHER INFORMATION: primer

<400> SEQUENCE: 13
gggcaaagaa gtcctccag                                             19
```

NUCLEIC ACID AMPLIFICATION IN THE PRESENCE OF MODIFIED RANDOMERS

RELATED APPLICATIONS

This application is a continuation of U.S. application Ser. No. 12/406,450 filed Mar. 18, 2009 and which claims priority to EP 08005100.6 filed Mar. 19, 2008.

FIELD OF THE INVENTION

The present invention relates to the field of template dependent polymerase catalyzed primer extension reactions. In particular, the invention provides a new method for nucleic acid amplification by means of performing a polymerase chain reaction (PCR). More precisely, the present invention provides a new method for performing a hot start PCR characterized in that unspecific primer dimer amplification is avoided.

BACKGROUND

A major problem with nucleic acid amplification and more especially with PCR is the generation of unspecific amplification products. In many cases, this is due to an unspecific oligonucleotide priming and subsequent primer extension event prior to the actual thermocycling procedure itself, since thermostable DNA polymerases are also moderately active at ambient temperature. For example, amplification products due to eventually by chance occurring primer dimerisation and subsequent extension are observed frequently. In order to overcome this problem, it is well known in the art to perform a so called "hot start" PCR, wherein one component essential for the amplification reaction is either separated from the reaction mixture or kept in an inactive state until the temperature of the reaction mixture is being raised for the first time. Since the polymerase cannot function under these conditions, there is no primer elongation during the period when the primers can bind non-specifically. In order to achieve this effect, several methods have been applied:

a) Physical Separation of the DNA Polymerase

The physical separation can be obtained for example by a barrier of solid wax, which separates the compartment containing the DNA polymerase from the compartment containing the bulk of the other reagents. During the first heating step the wax is then melting automatically and the fluid compartments are mixed (Chou, Q., et al., Nucleic Acids Res 20 (1992) 1717-23, U.S. Pat. No. 5,411,876). Alternatively, the DNA polymerase is affinity immobilized on a solid support prior to the amplification reaction and only released into the reaction mixture by a heat mediated release (Nilsson, J., et al., Biotechniques 22 (1997) 744-51). Both methods, however are time consuming and inconvenient to perform.

b) Chemical Modification of DNA Polymerase

For this type of hot start PCR, the DNA polymerase is reversibly inactivated as a result of a chemical modification. More precisely, heat labile blocking groups are introduced into the Taq DNA polymerase which renders the enzyme inactive at room temperature (U.S. Pat. No. 5,773,258). These blocking groups are removed at high temperature during a pre-PCR step such that the enzyme is becoming activated. Such a heat labile modification, for example can be obtained by coupling Citraconic Anhydride or Aconitric Anhydride to the Lysine residues of the enzyme (U.S. Pat. No. 5,677,152). Enzymes carrying such modifications are meanwhile commercially available as Amplitaq Gold (Moretti, T., et al., Biotechniques 25 (1998) 716-22) or FastStart DNA polymerase (Roche Molecular Biochemicals). However, the introduction of blocking groups is a chemical reaction which arbitrarily occurs on all sterically available Lysine residues of the enzyme. Therefore, the reproducibility and quality of chemically modified enzyme preparations may vary and can hardly be controlled.

c) Recombinant Modification of DNA Polymerase

Cold sensitive mutants of Taq Polymerase have been prepared by means of genetic engineering. These mutants differ from the wildtype enzyme in that they lack the N-terminus (U.S. Pat. No. 6,241,557). In contrast to native or wild type recombinant Taq Polymerase, these mutants are completely inactive below 35° C. and thus may be used in some cases for performing a hot start PCR. However, the N-terminal truncated cold sensitive mutant form requires low salt buffer conditions, has a lower processivity as compared to the wild type enzyme and thus can only be used for the amplification of short target nucleic acids. Moreover, since the truncated form lacks 5'-3' exonuclease activity, it can not be used for real time PCR experiments based on the TaqMan detection format.

d) DNA Polymerase Inhibition by Nucleic Acid Additives

Extension of non-specifically annealed primers has been shown to be inhibited by the addition of short double stranded DNA fragments (Kainz, P., et al., Biotechniques 28 (2000) 278-82). In this case, primer extension is inhibited at temperatures below the melting point of the short double stranded DNA fragment, but independent from the sequence of the competitor DNA itself. However, it is not known, to which extent the excess of competitor DNA influences the yield of the nucleic acid amplification reaction.

Alternatively, oligonucleotide Aptamers with a specific sequence resulting in a defined secondary structure may be used. Such Aptamers have been selected using the SELEX Technology for a very high affinity to the DNA polymerase (U.S. Pat. No. 5,693,502, Lin, Y., and Jayasena, S. D., J Mol Biol 271 (1997) 100-11). The presence of such Aptamers within the amplification mixture prior to the actual thermocycling process itself again results in a high affinity binding to the DNA polymerase and consequently a heat labile inhibition of its activity (U.S. Pat. No. 6,020,130). Due to the selection process, however, all so far available Aptamers can only be used in combination with one particular species of DNA polymerase.

e) Taq DNA Antibodies

An alternative approach to achieve heat labile inhibition of Taq DNA polymerase is the addition of monoclonal antibodies raised against the purified enzyme (Kellogg, D. E., et al., Biotechniques 16 (1994) 1134-7; Sharkey, D. J., et al., Biotechnology (NY) 12 (1994) 506-9). Like the oligonucleotide Aptamers, the antibody binds to Taq DNA polymerase with high affinity at ambient temperatures in an inhibitory manner (U.S. Pat. No. 5,338,671). The complex is resolved in a preheating step prior to the thermocycling process itself. This leads to a substantial time consuming prolongation of the amplification as a whole, especially if protocols for rapid thermocycling are applied (WO 97/46706).

U.S. Pat. No. 5,985,619 discloses a specific embodiment for performing PCR using a hot start antibody, wherein besides Taq polymerase, e.g. Exonuclease III from *E. coli* is added as a supplement to the amplification mixture in order to digest unspecific primer dimer intermediates. As disclosed above, Exonuclease III recognizes double-stranded DNA as a substrate, like, for example, target/primer- or target/primer extension product hybrids. Digestion is taking place by means of cleavage of the phosphodiester bond at the 5' end of the 3' terminal deoxynucleotide residue. Since this type of exonuclease is active at ambient temperatures, all unspecifically annealed primers and primer extension products therefore are digested. This results in some embodiments in an even enhanced specificity of the amplification reaction. Yet, digestion of the unspecific primers dependent on the duration of the preincubation time may lead to a substantial and uncontrolled decrease in primer concentration, which in turn may affect the amplification reaction itself.

f) Usage of Modified Primers Alone or in Combination with Exonucleases

EP 0 799 888 and GB 2293238 disclose an addition of 3' blocked oligonucleotides to PCR reactions. Due to the 3' block, these oligonucleotides can not act as primers. The blocked oligonucleotides are designed to compete/interact with the PCR primers which results in reduction of non-specific products.

Another alternative is the use of phosphorothioate oligonucleotide primers in combination with an exonuclease III in the PCR reaction mixes (EP 0 744 470). In this case, a 3' exonuclease, which usually accepts double stranded as well as single stranded DNA substrates, degrades duplex artifacts such as primer dimers as well as carry over amplicons, while leaving the single stranded amplification primers undegraded. Similarly, the usage of primers with a basic modified 3' end and template dependent removal by *E. coli* Endonuclease IV has been suggested (U.S. Pat. No. 5,792,607).

A particular embodiment of the general idea is found in EP 1 275 735. Its specification discloses a composition for performing a nucleic acid amplification reaction comprising (i) a thermostable DNA-Polymerase, (ii) a thermostable 3'-5' Exonuclease, and (iii) at least one primer for nucleic acid amplification with a modified 3' terminal residue which is not elongated by said thermostable DNA-Polymerase as well as methods for performing a PCR reaction using this composition.

However, it is major drawback of the disclosed alternatives that for each PCR reaction, modified primers are required, which lead to increased requirements regarding increase the cost for each individual assay.

g) Other PCR Additives

Other organic additives known in the art like DMSO, betaines, and formamides (WO 99/46400; Hengen, P. N., Trends Biochem Sci 22 (1997) 225-6; Chakrabarti, R., and Schutt, C. E., Nucleic Acids Res 29 (2001) 2377-81) result in an improvement of amplification of GC rich sequences, rather than prevention of primer dimer formation. Similarly, heparin may stimulate in vitro run-on transcription presumably by removal of proteins like histones in order to make chromosomal DNA accessible (Hildebrand, C. E., et al., Biochimica et Biophysica Acta 477 (1977) 295-311).

It is also known that addition of single strand binding protein (U.S. Pat. No. 5,449,603) or tRNA, (Sturzenbaum, S. R., Biotechniques 27 (1999) 50-2) results in non-covalent association of these additives to the primers. This association is disrupted when heating during PCR. It was also found that addition of DNA helicases prevent random annealing of primers (Kaboev, O. K., et al., Bioorg Khim 25 (1999) 398-400). Furthermore, poly-glutamate (WO 00/68411) in several cases may be used in order to inhibit polymerase activity at low temperatures.

Moreover, it is known that polyanionic polymerase inhibitors may control the activity of thermostable DNA polymerases dependent on the applied incubation temperature. U.S. Pat. No. 6,667,165 discloses a hot start embodiment, characterized in that inactive polymerase-inhibitor complexes are formed at temperatures below 40° C. Between 40° C. and 55° C., the inhibitor competes with the template DNA for binding to the Taq Polymerase, whereas at temperatures above 55° C., the inhibitor is displaced from the polymerase active site. Yet, the inhibitor tends to reduce the obtainable product yield, when primers with lower annealing temperatures are used.

h) Magnesium Sequestration

Since thermostable polymerases are known for a long time to be active only in presence of Mg2+ cations, a sequestration of magnesium prior to the start of the thermocycling protocol has been attempted in order to avoid mispriming and unspecifying primer extension. As disclosed in U.S. Pat. No. 6,403,341, Mg2+ may be present in form of a precipitate and thus unavailable at the beginning of the amplification reaction. Upon temperature increase during the first round of thermocycling, the precipitate dissolves and Mg2+ becomes fully available within the first 3 cycles. Such a solution has been shown to be fairly applicable and capable of providing good hot start results. On the other hand, such a solution does not allow the preparation of mastermixes containing all reagents except primer and target nucleic acid which are necessary to perform a nucleic acid amplification reaction. As a consequence, inter-assay data reproducibility and data comparisons are complicated.

In view of the outlined prior art it was an object of the invention to provide an improved alternative composition and method for hot start PCR, which allows for an inhibition of unspecific priming and primer extension not only prior to the amplification process itself but also during the thermocycling process. More precisely, it was an object of the invention to provide an alternative composition and method for hot start PCR, where no extension of non specifically annealed primers can take place.

SUMMARY OF THE INVENTION

Thus, in a first aspect, the present invention provides a composition comprising
  a DNA Polymerase
  Deoxynucleotides
  at least one primer oligonucleotide, and
  a randomized 5-8 mer oligonucleotide, characterized in that said oligonucleotide comprises a modification with an organic hydrophobic moiety.

Such a composition is particularly useful for the performance of a PCR amplification reaction, because formation of artificial amplification products such as primer dimers is avoided.

Preferably, said modification is positioned at the 5' end of said randomized oligonucleotide. Also preferably, said organic hydrophobic moiety of said modification is either a Pyrene or a Stilbene.

In one specific embodiment, the DNA Polymerase is a thermostable DNA Polymerase such as Taq Polymerase. If this is the case, the composition may comprise not only one primer but at least a pair of amplification primers.

In addition, it is also within the scope of the present invention, if any of the compositions as defined above further comprises a target nucleic acid sample.

In a second aspect, the present invention is directed to a kit comprising a DNA Polymerase, and a randomized 5-8 mer oligonucleotide, characterized in that said oligonucleotide comprises a modification with an organic hydrophobic moiety. Preferably, said modification is positioned at the 5' end of said randomized oligonucleotide (capped randomer). Also preferably, said organic hydrophobic moiety of said modification is either Pyrene or Stilbene.

In a specific embodiment, said kit is characterized in that said DNA polymerase is a thermostable DNA polymerase such as Taq DNA Polymerase. If this is the case, the kit may comprise not only one primer but at least a pair of amplification primers.

In a third aspect, the present invention provides a method for primer extension on a specific target nucleic acid comprising the steps of
providing a sample suspected to contain said target nucleic acid
adding any of the compositions as disclosed above, and performing at least a first primer extension reaction.

In particular, the present invention provides a method for amplification of a specific target nucleic acid comprising the steps of
providing a sample suspected to contain said target nucleic acid
adding a composition as disclosed above which comprises a thermostable DNA polymerase and a pair of amplification primers, and
performing a nucleic acid amplification reaction.

Preferably, said nucleic acid amplification reaction is a Polymerase Chain Reaction which is monitored in real time. In a particular embodiment, the amplification product generated by said amplification is subsequently subjected to a melting curve analysis.

DETAILED DESCRIPTION OF THE INVENTION

The present invention provides a new and improved solution for performing a primer extension reaction with increased specificity. In particular, the present invention provides a new and improved solution for performing a nucleic acid amplification reaction with improved specificity. The so called hot start effect results in effective inhibition of undesired primer elongations. Undesired primer elongations result from accidental hybridization events wherein primers are at least partially hybridized to any sequence in a nucleic acid sample which is different from the actual primer binding side of the nucleic acid target.

The present invention thus provides compositions comprising
a DNA Polymerase
Deoxynucleotides
at least one primer oligonucleotide, and
a randomized 5-8 mer oligonucleotide, characterized in that said oligonucleotide comprises a modification with an organic hydrophobic moiety.

The DNA Polymerase in general may be any enzyme which is capable of performing a template dependent primer extension reaction. Such a template dependent primer extension reaction can occur on all partially double stranded nucleic acid hybrids characterized in that a primer nucleic acid with a free 3' hydroxyl group is hybridized to a template nucleic acid with a single stranded 5' overhang. The template dependent polymerase then catalyzes extension of the 3' end of the primer by means of incorporating nucleotide residues which are always complementary to the nucleotide at the opposite position within the template strand. The reaction uses dNTPs as substrates and results in a release of pyrophosphate.

In one embodiment, said DNA Polymerase is an RNA template dependent Polymerase or any modification thereof. Such enzymes are usually called Reverse Transcriptase. Examples are AMV reverse transcriptase or MMLV reverse transcriptase. In particular, Transcriptor Reverse Transcriptase (Roche Applied Science cat. No: 03 531 317 001) is an applicable enzyme in the context of the present invention. Inventive compositions comprising such RNA dependent DNA Polymerase are especially useful for all kinds and applications of preparative and analytical cDNA syntheses, and in particular 2-step RT-PCR.

In another embodiment the DNA Polymerase is a DNA template dependent DNA polymerase or any mutant or modification thereof. One prominent example is Klenow polymerase (Roche Applied Science Cat. No. 11 008 404 001). Preferably, the DNA polymerase is a thermostable DNA polymerase or any mutant or modification thereof. A typical example is Taq DNA Polymerase from Thermus aquaticus (Roche Applied Science Cat. No: 11 647 679 001). The DNA dependent DNA polymerase enzymes may or may not have a 3'-5' proofreading activity such as Pwo Polymerase (Roche Applied Science Cat. No: 11 644 947 001). Furthermore the DNA polymerase component of the present invention may be a mix of enzymes with and without proofreading activity such as the Expand High Fidelity system (Roche Applied Science Cat. No: 11 732 641 001). Inventive compositions comprising any kind of thermostable Polymerase are specifically useful for performing various preparative or analytical embodiments of the Polymerase Chain Reaction (PCR).

In a further embodiment the DNA polymerase component of the present invention is a thermostable DNA dependent DNA polymerase with additional RNA template dependent Reverse Transcriptase activity like the Polymerase from Thermus thermophilus (Roche Applied Science Cat. No: 11 480 014 001) or a mix of a an RNA dependent DNA Polymerase (i.e. a reverse Reverse Transcriptase) and a thermostable DNA dependent DNA polymerase. Inventive compositions comprising such components are particularly useful for analytical performance of one-step RT-PCR.

The Deocxynucleotide-Triphosphates (dNTPs) are usually a mixture of dATP, dCTP, dGTP and dTTP, however, in some specific instances, only 3 or less different kinds of dNTP may be used. Morever, such a dNTP may be chemically modified in any way, as long as said building block is still capable of being incorporated into the nascent polynucleotide chain by the Polymerase. For example, said modified nucleotide compounds may carry a Biotin or a fluorescent compound modification at the respective base moiety.

The at least one primer oligonucleotide is usually a desoxy-oligonucleotide which is completely or almost completely complementary to a specific region of the target nucleic acid. Furthermore, said primer moiety must have a free 3' hydroxyl group so that it is extendible by a DNA polymerase. For specific purposes, such a primer may be chemically modified for example at its 3' end. Examples for frequently used modifications are Biotin labels, Digoxygenin labels and fluorescent labels.

If a thermostable DNA dependent DNA polymerase is designed for a PCR reaction, a composition according to the present invention comprises usually two primer oligonucleotides hybridizing in opposite orientations to the opposite strands of the target nucleic acid adjacent to the target sequence that shall become amplified. It is also possible that a composition of the present invention comprises multiple pairs of oligonucleotide PCR primers for multiplex PCR amplification.

The important compound that discriminates a composition according to the present invention from compositions that are currently used in the art is the addition of a randomized 5-8 mer oligonucleotide, characterized in that said oligonucleotide comprises a modification with an organic hydrophobic moiety. More exactly, the term "randomized oligonucleotide" refers to a pool of oligonucleotides, the sequences of which represent more or less equally all possible combinations of the 4 different nucleotide residues. Although the addition of 5 mers as well as the addition of 8 mers have been proven to have the desired hot start effect, it has turned out to be particular advantageous, if randomized hexamer oligonucleotides are being used. Said randomized oligonucleotides may be added to the primer extension reaction or the PCR reaction in a concentration range between 10 µM and 1 mM, preferably between 25 µM and 400 µM and most preferably in a concentration of about 10 µM. It has also been proven to be particular advantageous, if the randomized oligonucleotides have a non extendible 3' terminus, which for example may be blocked by a phosphate moiety. This avoids an undesired elongation by the Polymerase in case of an accidential hybridization of any of the oligonucleotides at any region of the sample nucleic acid.

The randomized oligonucleotides are chemically modified with an organic hydrophobic moiety. Said moieties usually do not interfere with any type of primer extension reaction. For example, such an organic hydrophobic moiety may be selected from a group of moieties consisting of polycondensend aromatic and heteroaromatic rings like naphthalin, anthracen, phenantren, pyrene, anthraquinones, carbazol phenantrolines, quonolines, etc. or from stilbens, or from steroids like cholesterol. Such hydrophobic moieties may be substituted by non bulky substituents like cyano, methoxy, methyl, nitro and halogens, and are partially known to act as a so called "cap" for stabilizing terminal base pairs. Narayanan, S., et al., Nucleic Acids Research 32(9) (2004) 2901-2911; Dogan, Z., et al., Journal of the American Chemical Society 126(15) (2004) 4762-4763.

Most preferably, such an organic hydrophobic moiety is either a an optionally substituted Pyrene or a an optionally substituted Stilben, which have the following chemical structures:

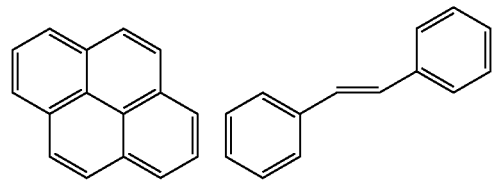

Most preferably such a pyrene or stilbene is attached to the 5' end of a randomized oligonucleotide whereas the 5' end of such an oligonucleotide has the following structure

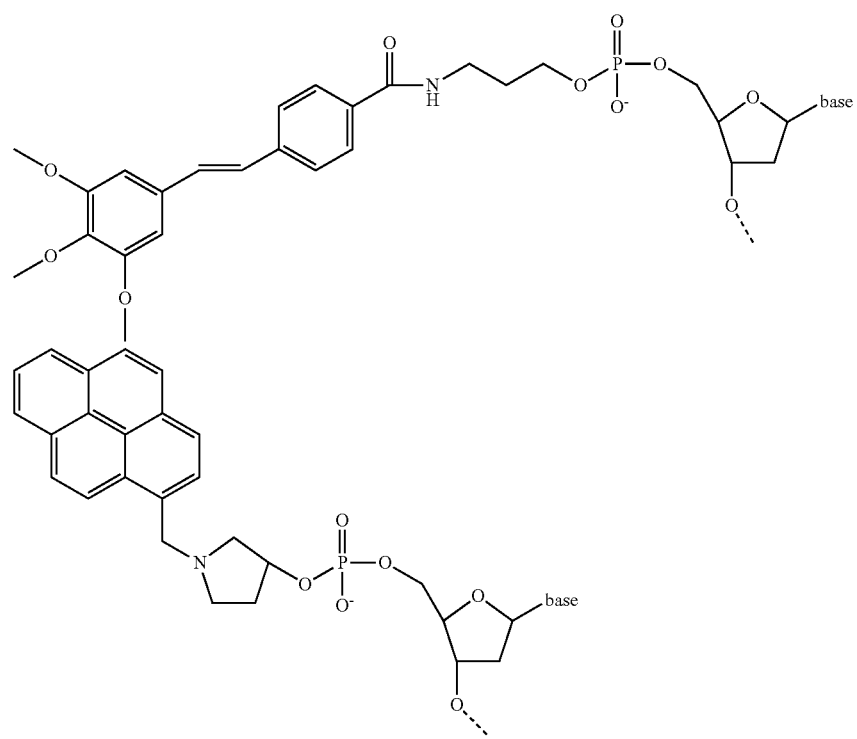

The organic hydrophobic moiety can be positioned at any part of the randomized oligonucleotide. Preferably however, said modification is introduced at the 5' end of the randomized oligonucleotide. The reason is that such 5' modification can be introduced into the oligonucleotide using Phosphoramidite chemistry with an appropriate terminal Phosphoramidite according to standard methods that are well known in the art and that pyrene and stilbene phosphoramidites are commercially available.

The randomized oligonucleotide could comprise nucleobase analogs with modified bases like 7 deaza analogs like 7 deaza dG, 7 deaza 8 aza analogs like 7 bromo 7 deaza 8 aza 2 amino dA, or substituted bases like propinyl U, propinyl C, or analogs with modified sugars like 2' methoxy ribose or locked sugars like in LNA, or with ribose analogs like hexitol and altritol. Instead of randomization universal bases like nitroindol or N8 ribosylated-7 deaza 8 aza dA are used whereas preferably only at one position of the randomer is used a universal base instead of randomers. The internucleosidic phosphate could be substituted by an phosphate mimetikum like phosphorthioate or methyl phosphonate or phosphoramidates. The randomized oligonucleotide has preferably one hydrophobic moiety but can be additionally substituted by other hydrophobic moieties, whereas the hydrophobic moieties are independently selected from each other.

Those compositions which comprise randomized oligonucleotides that are chemically modified with an organic hydrophobic moiety in conjunction with a DNA dependent thermostable DNA polymerase and at least one pair of amplification primers are particularly useful for the performance of a PCR amplification reaction. The reason is that the presence of said randomized and modified oligonucleotides efficiently inhibits formation of artificial amplification products such as primer dimers at temperatures below the annealing temperatures of the respective amplification primers, thereby creating a hot start effect.

It is also within the scope of the present invention, if any of the compositions as defined above further comprises a target nucleic acid sample. The sample usually may for example contain genomic DNA or fragmented genomic DNA in conjunction with DNA dependent DNA polymerases or total cellular or poly-A+ RNA in conjunction with RNA dependent DNA polymerases.

In one particular aspect, the present invention also provides kits for preparing compositions as disclosed in detail above. Thus, the present invention is also directed to a kit comprising at least a DNA Polymerase and a randomized 5-8 mer oligonucleotide, characterized in that said oligonucleotide comprises a modification with an organic hydrophobic moiety. Preferably, said modification is any of the examples as disclosed above and is positioned at the 5' end of said randomized oligonucleotide. In addition, the kits may comprise further components such as Desoxynucleotide Triphosphates (dNTPs) and appropriate buffers as well as other reagent additives, which are useful for performing respective primer extension reactions. Furthermore, parameter specific kits may comprise at least one target specific primer oligonucleotide.

In a first specific embodiment, the kit is designed for cDNA synthesis and comprises a Reverse Transcriptase as disclosed above. As a primer component, the kit may comprise either a parameter specific primer for amplification of specific cDNAs.

In a second specific embodiment, the kit is designed for performing PCR and comprises a DNA dependent thermostable Polymerase or a mix of DNA dependent thermostable Polymerases. The kit may then additionally comprise for example dNTPs and/or a buffer solution and/or at least one or multiple pairs of amplification primers. More specifically, if the kit is designed for one-step RT-PCR, the enzyme component may be a DNA dependent thermostable DNA polymerase which in addition comprises Reverse Transcriptase activity.

In a third specific embodiment, the kit is designed for 2-step RT-PCR and may comprise various combinations of components selected from the components of the first and second embodiment as disclosed above.

In addition, kits according to the second and third specific embodiments may comprise components which are useful for the detection of PCR amplification products. For example, if the kit is designed for Real Time PCR (=qPCR), such a kit may additionally comprise a double stranded DNA binding dye component such as SybrGreen (Roche Applied Science Cat. No: 04 707 516 001) or the LC480 ResoLight dye (Roche Applied Science Cat. No: 04 909 640 001). Alternatively, such a kit may additionally comprise fluorescently labeled hybridization probes such as TaqMan probes (U.S. Pat. No. 5,804,375), Molecular Beacons (U.S. Pat. No. 5,118,801), FRET hybridization probes (U.S. Pat. No. 6,174,670), or Simple Probes (WO 02/14555).

The present invention is not only directed to compositions and kits but also to methods of performing primer extension reactions in general and PCR or reverse transcription reactions in particular. Thus, in its broadest sense, a method according to the present invention comprises the steps of providing a sample suspected to contain said target nucleic acid adding any of the compositions as disclosed above, and performing at least a first primer extension reaction.

More precisely, a method according to the present invention comprises the steps of providing a sample suspected to contain said target nucleic acid adding a DNA Polymerase Deoxynucleotides at least one primer oligonucleotide, and a randomized 5-8 mer oligonucleotide, characterized in that said oligonucleotide comprises a modification with an organic hydrophobic moiety.

performing at least a first primer extension reaction.

In a first embodiment, the sample is either total or poly-A+ RNA, the DNA Polymerase is a Reverse Transcriptase and the primer oligonucleotide is a specific primer that is complementary to a specific type of cDNA.

In a second embodiment, the sample is derived from genomic DNA, the DNA Polymerase is a thermostable DNA Polymerase or a mixture of thermostable DNA polymerases and at least one pair or multiple pairs of amplification primers are added prior to a PCR amplification reaction. Preferably, said nucleic acid amplification reaction is a Polymerase Chain Reaction which is monitored in real time according to standard methods known in the art (see, for example U.S. Pat. No. 5,210,015, U.S. Pat. No. 5,338,848, U.S. Pat. No. 5,487,972, WO 97/46707, WO 97/46712, WO 97/46714).

In a particular embodiment, the amplification product generated is subjected to a melting curve analysis (U.S. Pat. No. 6,174,670, U.S. Pat. No. 6,569,627) by means of subjecting the amplification product to a thermal gradient over time. In this type of experiment, fluorescence intensity is monitored, which is due either to the binding of a respectively labeled hybridization probe, or due to the fluorescence originating from a DNA binding dye. Then, the first derivative of the decrease in fluorescence intensity due to the melting of the hybridization probe or the two strands of amplicon, respectively, is plotted against the temperature gradient. As it will be shown in the examples, the presence of a randomized 5-8 mer oligonucleotide, characterized in that said oligonucleotide comprises a modification with an organic hydrophobic moiety during the amplification process subsequently provides superior quality melting curve results.

Summarizing, it can be stated the inventive method comprises several advantages over methods already disclosed in the art. The presence of a randomized 5-8 mer oligonucleotide, characterized in that said oligonucleotide comprises a modification with an organic hydrophobic moiety during a primer extension reaction such as a reverse transcription or a PCR or an RT-PCR clearly results in an increase in the specificity of the respective reaction.

To date, the inventors do not completely understand the reason or reasons for this positive effect. One possible mechanistic explanation might be that at low temperatures, a part of the randomized population of oligonucleotide molecules may interact with the primer to an extend that the primer is not capable of being elongated even if it is already annealed to a longer, substantially complementary nucleic acid molecule.

One major advantage of the present invention is the ease of use and the short activation time to eliminate the inhibition of the polymerase at low temperatures. Simply, a randomized 5-8 mer oligonucleotide, characterized in that said oligonucleotide comprises a modification with an organic hydrophobic moiety needs to be added to a PCR reaction set up. During PCR thermocycling the denaturation time prior to the first cycle which is usually required to separate double stranded DNA templates into single strands is sufficient to eliminate the interaction between the conjugated randomers and the PCR primers.

Furthermore, random hexamers can be synthesized according to standard phosphoramidate chemistry methods which are well established in the art. Moreover, also 5' modifications can be introduced into the oligonucleotide using Phosphoramidate chemistry with a respectively modified terminal Phosphoramidate according to standard methods very easily. Thus the production costs for the inventive PCR additive are fairly low as compared to other hot start solutions.

In addition, the inventive methods, compositions and kits can be generically used for any kind of primer extension, reverse transcription or PCR amplification, irrespective of what specific target nucleic acid sequence shall be prepared, amplified, detected, or analyzed.

BRIEF DESCRIPTION OF THE FIGURES

FIG. 4a PCR on various amounts of genomic DNA and melting curve analysis without Pyren capped hexamers FIG. 4b PCR on various amounts of genomic DNA and melting curve analysis with Pyren capped hexamers FIG. 5 Real time RT PCR according to example 9
  5a: First strand cDNA synthesis in the presence of capped hexamers, and subsequent PCR in the absence of capped hexamer,
  5b: First strand cDNA synthesis in the presence of capped hexamers, and subsequent PCR in the presence of capped hexamer,
  5c: First strand cDNA synthesis in the absence of capped hexamers, and subsequent PCR in the absence of capped hexamer,
  5d: First strand cDNA synthesis in the absence of capped hexamer, and subsequent PCR in the presence of capped hexamer.

The following examples, sequence listing and figures are provided to aid the understanding of the present invention, the true scope of which is set forth in the appended claims. It is understood that modifications can be made in the procedures set forth without departing from the spirit of the invention.

EXAMPLES

Randomized oligonucleotides are synthesized by standard methods on a ABI 394 synthesizer on a 10 μmol scale in the trityl off mode using commercially available phosphate CPG (2-[2-(4,4'-Dimethoxytrityoxy)ethylsulfonyl]ethyl-2-succinoyl)-long chain alkylamino-CPG) as solid support and a aequimolare (Σ0.1 mol) mixture of a standard dA(bz) dT, dG (iBu) dC(Bz) phosphoramidites, deprotection was performed under standard conditions with ammonia or NaOH and the product was desalted via dialysis

Example 1

5' Pyrene-capped hexamers were analyzed in DNA amplification. PCR reactions in the presence or absence of 100 μM Pyrene-capped hexamers were performed in 50 μl reactions containing 50 ng, 25 ng, 10 ng, 5 ng, 1 ng and 0 ng of human genomic DNA, 30 mM Tris-HCl, pH 8.6, 1.5 mM $MgCl_2$, 50 mM KCl, 0.2 mM dNTP's each, 0.4 μM primers (SEQ ID NO: 1 ATT AGA GAA CCA TGT TAA CAC TAC CG and SEQ ID NO: 2 GAG GTG AAT GAC CAC TGT TTA TTT TC) and 2.5 units Taq DNA polymerase. The following cycle conditions were used: Initial denaturation for 4 min at 94° C. and 35 cycles with 20 seconds denaturation at 94° C., 30 seconds annealing at 62° C., 60 seconds elongation at 72° C. and a final elongation step of 7 min at 72° C. The amplification products were separated on an agarose gel and visualized by ethidium bromide staining.

Figure 1:
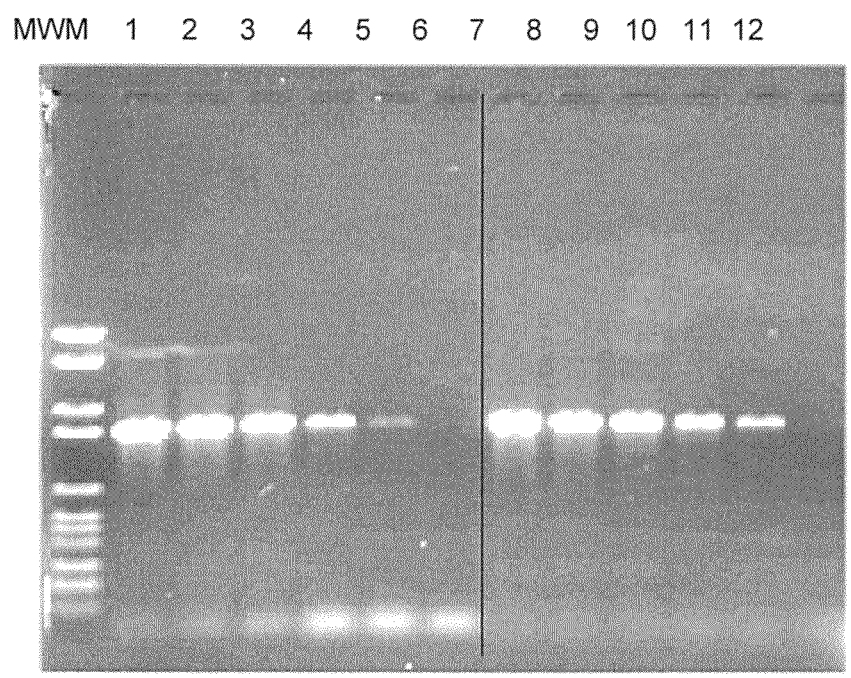
FIG. 1 Amplification of genomic DNA in the presence of Pyrene-capped hexamers according to example 1
  Lane 1: PCR without additive, 50 ng DNA
  Lane 2: PCR without additive, 25 ng DNA
  Lane 3: PCR without additive, 10 ng DNA
  Lane 4: PCR without additive, 5 ng DNA
  Lane 5: PCR without additive, 1 ng DNA
  Lane 6: PCR without additive, no template control
  Lane 7: PCR with additive, 50 ng DNA
  Lane 8: PCR with additive, 25 ng DNA
  Lane 9: PCR with additive, 10 ng DNA
  Lane 10: PCR with additive, 5 ng DNA
  Lane 11: PCR with additive, 1 ng DNA
  Lane 12: PCR with additive, no template control FIG. 2 Amplification of genomic DNA in the presence of Pyrene-capped hexamers according to example 2
  Lane 1: Taq polymerase, 30 ng DNA
  Lane 2: Taq polymerase, 3 ng DNA
  Lane 3: Taq polymerase, 0.3 ng DNA
  Lane 4: Taq polymerase, pyrene-capped hexamers, 30 ng DNA
  Lane 5: Taq polymerase, pyrene-capped hexamers, 3 ng DNA
  Lane 6: Taq polymerase, pyrene-capped hexamers, 0.3 ng DNA FIG. 3 Amplification in the of pyrene or stilbene-capped octamers according to example 4
  Lanes 1 to 6: PCR products formed in the absence of additive with 50 ng, 25 ng, 10 ng, 5 ng, 1 ng and 0 ng of human DNA, respectively.
  Lanes 7 to 12: PCR products formed in the presence of 100 M pyrene-capped octamers with 50 ng, 25 ng, 10 ng, 5 ng, 1 ng and 0 ng of human DNA, respectively.
  Lanes 13 to 18: PCR products formed in the presence of 100 M stilbene-capped octamers with 50 ng, 25 ng, 10 ng, 5 ng, 1 ng and 0 ng of human DNA, respectively.

The result depicted in FIG. 1 shows a clear improvement in amplification specificity in the presence of pyrene-capped hexamers.

Example 2

Figure 2:
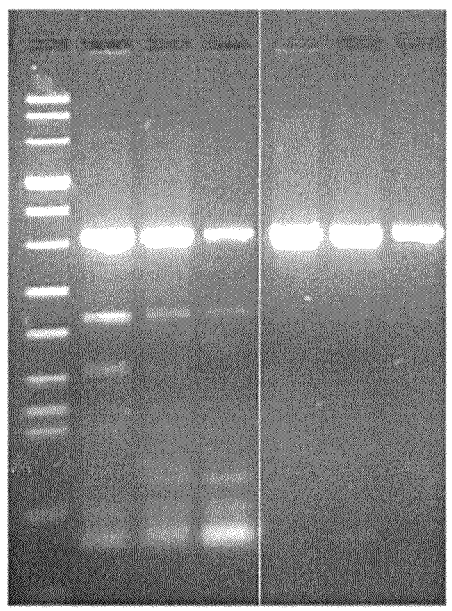

5' Pyrene-capped hexamers were analyzed in realtime PCR. PCR reactions in the presence or absence of Pyrene-capped hexamers were performed in 20 μl rections containing 30 ng, 3 ng or 0.3 ng of human genomic DNA, 50 mM Tris-HCl, pH 8.6, 0.2 mM CHAPS, 1 mM BigChap, 20 mM KCl, 3 mM $MgCl_2$, 0.4 μM primers (SEQ ID NO: 3 GGA AGT ACA GCT CAG AGT TCT GC and SEQ ID NO: 4 GAA TCT CCA TTC ATT CTC AAA AGG ACT), 0.2 mM deoxynucleotides, and 2.5 units Taq DNA polymerase. PCR was performed in a LIGHTCYCLER 480 Instrument (Roche Diagnostics GmbH) with the following cycle conditions: Initial denaturation for 2 min at 95° C. and 45 cycles with 1 second denaturation at 95° C., 10 seconds annealing at 65° C. and 10 seconds elongation at 72° C. The amplification products were separated on agarose gel and visualized by ethidium bromide staining (FIG. 2). The result shows a clear improvement in amplification specificity by pyrene-capped hexamers.

Example 3

5' Pyrene-capped pentamers were analyzed in the same experimental setup as described in example 2. The final concentrations tested were 50 µM, 100 µM, 150 µM and 200 µM. A variety of PCR products were formed in the control reaction (absence of additive), whereas in the presence of increasing amounts of pyrene-capped pentamers the desired product was formed with increased yield. Specificity and sensitivity were significantly higher than in the control experiment without additives (not shown).

Example 4

5' Pyrene-capped octamers and stilbene-capped octamers were tested in 100 µM final concentration in the amplification of a human collagen gene fragment with 50 ng, 25 ng, 10 ng, 5 ng, 1 ng and 0 ng of human DNA using the same PCR buffer as described in example 1. PCR primers (SEQ ID NO: 5 TAA AGG GTC ACC GTG GCT TC and SEQ ID NO: 6 CGA ACC ACA TTG GCA TCA) were used in 0.4 µM concentration. The total reaction volume was 50 µl. PCR cycling was performed in a block cycler with an initial denaturation for 4 min at 94° C., 35 cycles with 20 seconds at 94° C., 30 seconds at 62° C., 4 min at 72° C. and a final elongation step at 72° C. for 7 minutes.

Figure 3:
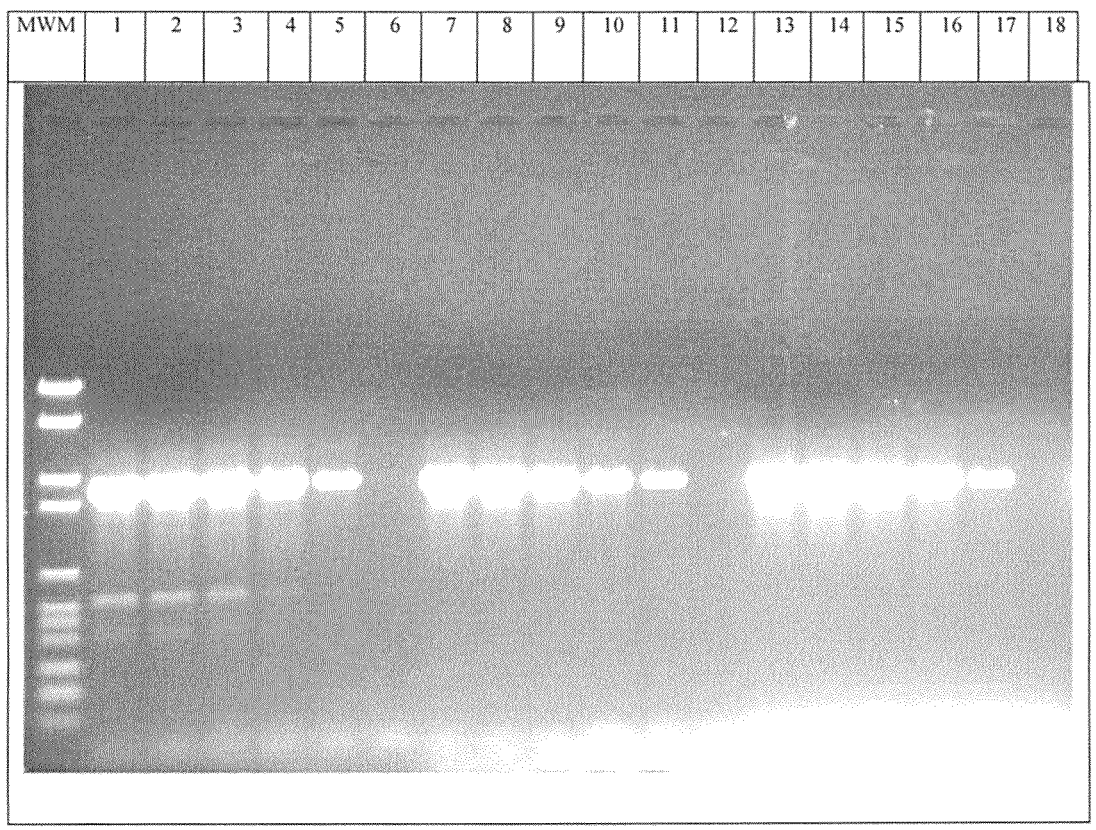

The result is depicted in FIG. 3. In the absence of additive an unspecific product of approximately 550 bp is formed. The unspecific product is not observed in the presence of capped oligonucleotides. Stilbene-capped octamers lead to a strong fluorescence at the bottom of the gel.

Example 5

5' Pyrene-capped monomers were analyzed in realtime PCR. PCR reactions in the presence or absence of pyrene-capped monomers (up to 400 µM) or pyrene-capped hexamers (up to 400 µM) were performed in 20 µl reactions containing 30 ng, 3 ng, 0.3 ng, 0.03 ng, 0.01 ng and 0 ng of human genomic DNA, 50 mM Tris-HCl, pH 8.6, 0.2 mM CHAPS, 1 mM BigChap, 20 mM KCl, 3 mM MgCl$_2$, 0.4 µM primers (SEQ ID NO: 7 CAC CCC GTG CTG CTG ACC GA and SEQ ID NO: 8 AGG GAG GCG GCC ACC AGA AG), 0.2 mM deoxynucleotides, and 2.5 units Taq DNA polymerase. PCR was performed in a LIGHTCYCLER 480 Instrument with the following cycle conditions: Initial denaturation for 2 minutes at 95° C. and 45 cycles with 1 second denaturation at 95° C., 15 seconds annealing at 65° C. and 5 seconds elongation at 72° C. The amplification products were separated on agarose gel and visualized by ethidium bromide staining The results show a clear improvement in amplification specificity by pyrene-capped hexamers, but no increase in specificity with pyrene-capped monomer in comparison to the control reaction (not shown).

Example 6

3' phosphorylated hexamers without organic molecule at the 5'end were tested in up to 200 µM final concentration in the amplification of a human collagen gene fragment with 50 ng, 25 ng, 10 ng, 5 ng, 1 ng and 0 ng of human genomic DNA using the same PCR buffer as described in example 1. PCR primers (SEQ ID NO: 5 TAA AGG GTC ACC GTG GCT TC and SEQ ID NO: 6 CGA ACC ACA TTG GCA TCA TC) were used in 0.4 µM final concentration. The total reaction volume was 50 µl. PCR cycling was performed in a block cycler with an initial denaturation for 4 minutes at 94° C., 35 cycles with 20 seconds at 94° C., 30 seconds at 58° C., 4 min at 72° C. and a final elongation step at 72° C. for 7 minutes. The amplification products were separated on an agarose gel and visualized by ethidium bromide staining. The results show no difference in PCR product compositions no matter whether hexamers were present or not (not shown).

Example 7

Figure 4:
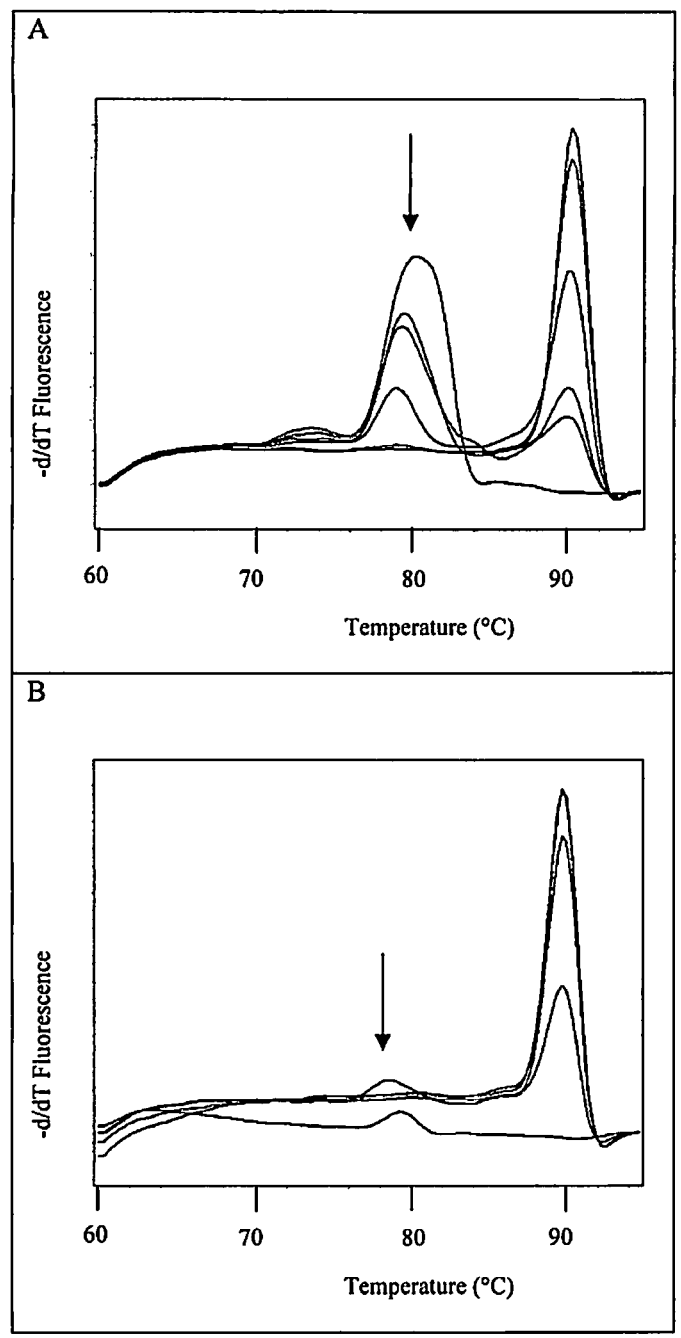
FIG. 4 Real time PCR melting curve analysis according to example 7
Figure 5:
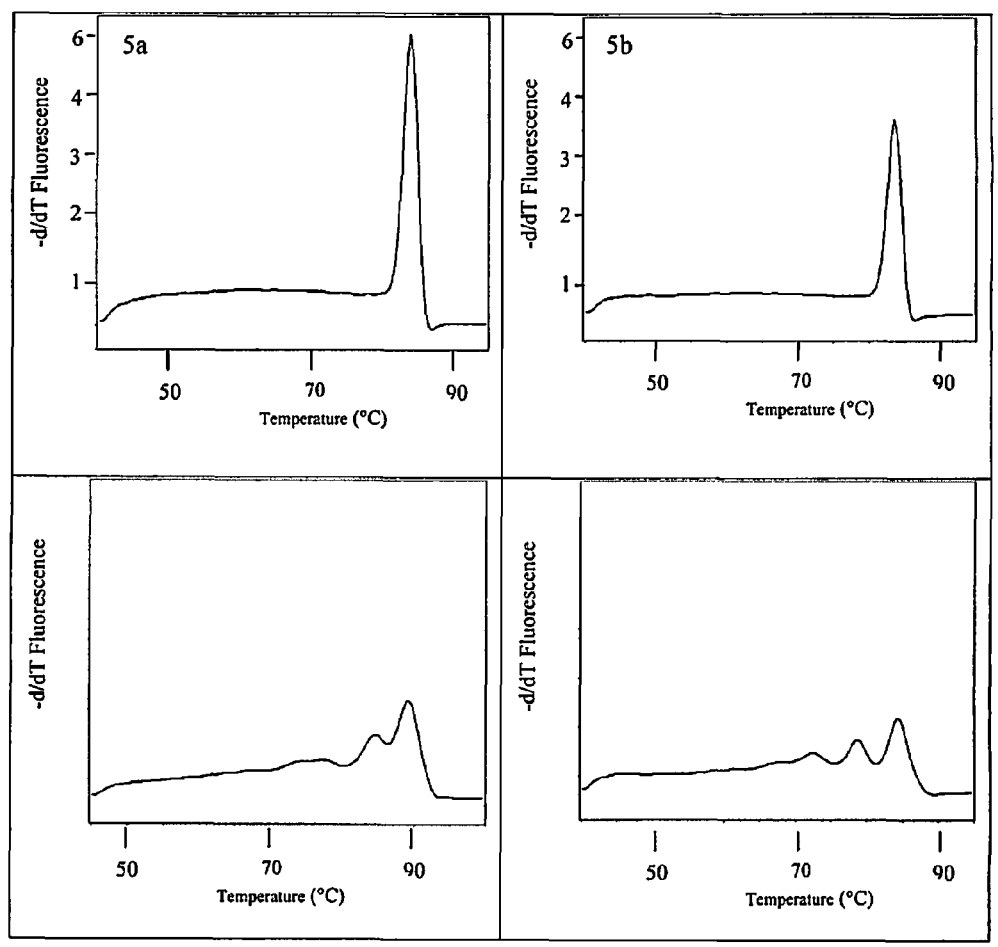

5' Pyrene-capped hexamers were analyzed in real time PCR. PCR reactions in the presence or absence of Pyrene-capped hexamers were performed in 20 µl reactions containing 30 ng, 3 ng or 0.3 ng, 0.03 ng, 0.01 ng and 0 ng of human genomic DNA, 50 mM Tris-HCl, pH 8.6, 0.2 mM CHAPS, 1 mM BigChap, 20 mM KCl, 3 mM MgCl$_2$, 0.4 µM primer (SEQ ID NO: 3 GGA AGT ACA GCT CAG AGT TCT GC and SEQ ID NO: 4 GAA TCT CCA TTC ATT CTC AAA AGG ACT), 0.2 mM deoxynucleotides, and 2.5 units Taq DNA polymerase and SYBR Green (1:40 000). PCR was performed in a LIGHTCYCLER 480 Instrument with the following cycle conditions: Initial denaturation for 2 min at 95° C. and 45 Cycles with 1 second denaturation at 95° C., 10 sec annealing at 65° C. and 10 seconds elongation at 72° C. For relative quantification of specific and unspecific products melting curves were performed according to the protocol recommended for LightCycler 480. The result is shown in FIG. 4. In the absence of additive (FIG. 4A) a high amount of unspecific product is formed, in the presence of additive (FIG. 4B) unspecific product is strongly reduced.

Example 8

In order to test whether 5' pyrene-capped hexamers can also be used in RT-PCR, with another DNA polymerase and whether the additive influences the cp-values of the PCR reaction. Therefore we performed an RT-PCR reaction using the Tth-polymerase based LIGHTCYCLER 480 RNA Master Hydrolysis Probes (Roche Applied Science, Cat No 04991885001). The reaction mixtures of 20 µl contained total RNA from human liver cells 100 pg, 10 pg, 1 pg, 0.1 pg and 0 pg, respectively, 7.4 µl RNA Master, 3.25 mM Manganese acetate, 0.5 µM of each primer (SEQ ID NO: 9 TGCAGC-CTCCATAACCATGAG and SEQ ID NO: 10 GATGCCT-GCCATTGGACCTA) and 0.25 µM hydrolysis probe (SEQ ID NO: 11 FAM-GATGCCTGCCATTGGACCTA-TAMRA). The reactions were performed in the absence of pyrene-capped hexamers or with 50 µM, 100 µM or 200 µM pyrene-capped hexamers. RT-PCR was performed in a LIGHTCYCLER 480 instrument according to the protocol recommended by the manufacturer. The cp-values are shown in Table 1. Pyrene-capped hexamers had no influence on crossing points. There is no delay in amplification signals or loss of sensitivity

TABLE 1

| RNA concentration | Crossing point of PCR product | | | |
|---|---|---|---|---|
| (pg/20 μl) | No additive | 50 μM | 100 μM | 200 μM |
| 100 | 32.06 | 32.06 | 32.21 | 31.90 |
| 10 | 35.73 | 34.91 | 35.77 | 35.56 |
| 1 | 38.05 | 38.02 | 38.02 | 38.85 |
| 0.1 | — | — | — | — |

Example 9

In order to evaluate whether the increase of specificity can also be observed in cDNA synthesis we performed a two-step RT-PCR experiment in a reaction set up close to the conditions of one-step RT-PCR. Four reactions were performed in parallel:

(a) first strand cDNA synthesis without capped random hexamers, and subsequent PCR in the presence of capped random hexamers, (b) first strand cDNA synthesis without 5' capped random hexamers, and subsequent PCR in the absence of capped random hexamers, (c) first strand cDNA synthesis in the presence of 5' capped random hexamers, and subsequent PCR in the absence of capped random hexamers, (d) first strand cDNA synthesis in the presence of 5' capped random hexamers, and subsequent PCR in the presence of capped random hexamers.

A primer pair was chosen which causes the formation of unspecific products when low amounts of RNA are present in the RT-PCR reaction: G6PDH forw (SEQ ID NO: 12 GCA AAC AGA GTG AGC CCT TC) and G6PDH rev (SEQ ID NO: 13 GGG CAA AGA AGT CCT CCA G) primers. cDNA was synthesized in 20 μl reactions containing 0.5 μM primers, 0.6 units of Transcriptor (Roche Applied Sciences, Cat No.: 03531317001), 30 mM Tris.HCl, pH 8.6; 3 mM $MgCl_2$, 200 μM dATP, 200 μM dGTP, 200 μM dCTP, 600 μM dUTP, 20 mM KCl, 0.2 mM CHAPSO, 1 mM BigChap, 125 ng/ml T4gene 32 protein, SYBR Green in a final dilution of 1:20 000 and 10 pg of total. RNA from HeLa cells. Two samples for cDNA synthesis were prepared, one with 100 μM pyrene-capped hexamer, the other without pyrene-capped hexamer. The reactions were incubated for 10 min at 50° C., 2 min at 95° C. and chilled on ice. PCR was performed in 20 μl reaction volumes using 2 μl of the cDNA reaction mixtures, 0.5 μM of the primers, 1.2 units of Taq polymerase in the same buffer as described for the cDNA reaction mixture in the presence or absence of additional pyrene-capped hexamer in 100 μM final concentration. The reactions were incubated in a LightCycler 480 instrument at 95° C. for 2 min and 45 cycles of 95° C./10 seconds, 60° C./10 seconds, 72° C./13 seconds. The melting profiles of the amplification products are shown in FIG. 5a-d. In the reactions where Pyrene-capped hexamer was present during cDNA synthesis (5a and 5b) one single product was formed with the melting point expected. When cDNA synthesis was performed in the absence of pyrene-capped hexamer (5c and 5d) several products were generated which have melting temperatures different to that of the specific product. This result shows that pyrene-capped hexamer is able to suppress unspecific product formation during reverse transcription of RNA.

Example 10

100 μM 5' Pyrene-capped hexamer with a 6 base pair overlap to the 3'end of one of the primers (Pyren-CGGTAG-3'phosphate) was analyzed in parallel to 100 μM 5' Pyrene-capped hexamer non complementary to the primers (Pyrene-CMTA-3"phosphate) in DNA amplification. In 50 μl reactions containing 50 ng, 25 ng, 10 ng, 5 ng, 1 ng and 0 ng of human genomic DNA, 30 mM Tris-HCl, pH 8.6, 1.5 mM $MgCl_2$, 50 mM KCl, 0.2 mM dNTP's each, 0.4 μM primer (SEQ ID NO: 1 ATT AGA GAA CCA TGT TAA CAC TAC CG and SEQ ID NO: 2 GAG GTG AAT GAC CAC TGT TTA TTT TC) and 2.5 units Taq DNA polymerase. PCR was performed in a block cycler with the following cycle conditions: Initial denaturation for 4 min at 94° C. and 35 Cycles with 20 seconds denaturation at 94° C., 30 seconds annealing at 62° C., 60 seconds elongation at 72° C. and a final elongation step of 7 minutes at 72° C. The amplification products were separated on an agarose gel and visualized by ethidium bromide staining. A control reaction in the absence of additive was run in parallel. In the presence of Pyrene-CGGTAG-3'phosphate no PCR product was detectable. In the samples which contained the non complementary Pyrene-CTTTTA-phosphate similar product yield and sensitivity was achieved as in the control reaction (in the absence of any additive).

What is claimed is:

1. A method for polymerase chain reaction (PCR) amplification of a specific target nucleic acid comprising the steps of providing a sample suspected of containing the target nucleic acid, adding a composition comprising a DNA polymerase, deoxynucleotides, at least one primer oligonucleotide, and a randomized 5-8 mer oligonucleotide, wherein said randomized oligonucleotide comprises a modification with an organic hydrophobic moiety selected from a pyrene or a stilbene, wherein said modification is positioned at the 5' end of said randomized oligonucleotide and performing at least a first primer extension reaction.

2. The method for PCR amplification of a specific target nucleic acid according to claim 1 wherein the DNA polymerase is thermostable and the composition further comprises a pair of amplification primers, and performing a nucleic acid amplification reaction.

3. The method according to claim 2, wherein said nucleic acid amplification reaction is a polymerase chain reaction which is monitored in real time.

4. The method according to claim 1 wherein an amplification product generated by said amplification is subjected to a melting curve analysis.

5. The method for PCR amplification according to claim 1 wherein the composition further comprises a target nucleic acid sample.

6. The method for PCR amplification according to claim 1, wherein the randomized oligonucleotide are present in the composition in a concentration of between 10 µM and 1 mM.

7. The method for PCR amplification according to claim 1, wherein the randomized oligonucleotide are present in the composition in a concentration of between 25 µM and 400 µM.

8. The method for PCR amplification according to claim 1, wherein the randomized oligonucleotide have a non-extendible 3' terminus.

9. The method for PCR amplification according to claim 1, wherein the randomized oligonucleotide consists of 5' pyrene-capped hexamers.

* * * * *